US008022256B2

(12) United States Patent
Caers et al.

(10) Patent No.: US 8,022,256 B2
(45) Date of Patent: *Sep. 20, 2011

(54) HYDROFORMYLATION OF BUTENES COMPRISING ISOBUTYLENE

(75) Inventors: Raphael F. Caers, Edegem (BE); Eddy Theophile Van Driessche, Eeklo (BE); Hubertus J. Beckers, Keerbergen (BE); Luc Roger Marc Martens, Meise (BE); Georges Maria Mathys, Bierbeck (BE); John Richard Shutt, Merchtem (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 160 days.

This patent is subject to a terminal disclaimer.

(21) Appl. No.: 10/572,011

(22) PCT Filed: Sep. 17, 2004

(86) PCT No.: PCT/EP2004/010622
§ 371 (c)(1),
(2), (4) Date: Nov. 29, 2006

(87) PCT Pub. No.: WO2005/028407
PCT Pub. Date: Mar. 31, 2005

(65) Prior Publication Data
US 2007/0112220 A1  May 17, 2007

(30) Foreign Application Priority Data
Sep. 23, 2003  (GB) .................................. 0322247.8

(51) Int. Cl.
C07C 45/00  (2006.01)
(52) U.S. Cl. ........................... 568/454; 568/451
(58) Field of Classification Search .................. 568/451, 568/454
See application file for complete search history.

(56) References Cited

U.S. PATENT DOCUMENTS

| 4,287,370 A | * | 9/1981 | Harris et al. .................. 568/454 |
| 4,426,542 A | | 1/1984 | Barker et al. |
| 4,482,749 A | | 11/1984 | Dennis et al. |
| 4,668,651 A | | 5/1987 | Billig et al. |
| 4,769,498 A | | 9/1988 | Billig et al. |
| 4,969,953 A | * | 11/1990 | Miyazawa et al. ............. 106/311 |
| 5,288,918 A | | 2/1994 | Maher et al. |
| 5,364,950 A | * | 11/1994 | Babin et al. ........................ 556/2 |
| 6,100,432 A | | 8/2000 | Borgel et al. |
| 6,340,778 B1 | | 1/2002 | Bueschken et al. |
| 6,403,837 B1 | | 6/2002 | Hess et al. |
| 6,555,716 B2 | | 4/2003 | Protzmann et al. |
| 6,770,791 B2 | | 8/2004 | Mathys et al. |
| 6,784,330 B2 | | 8/2004 | Brown et al. |
| 2001/0003785 A1 | * | 6/2001 | Protzmann et al. ........... 568/451 |
| 2003/0022947 A1 | | 1/2003 | McAtee et al. |
| 2004/0249218 A1 | | 12/2004 | Wiese et al. |

FOREIGN PATENT DOCUMENTS

| EP | 0016286 | 6/1983 |
| WO | WO 2005/028407 | 3/2005 |

OTHER PUBLICATIONS

American Chemistry Council, Olefins Panel, HPV Implementation Task Group: *High Production Volume (HPV) Chemical Challenge Program: Test Plan for the Low 1,3-Butadiene C4 Category*; Publication Date Jul. 9, 2001; pp. 5-26.
Scheidmeir W. J.: "Hydroformylierung Von Butenen Und Pentenen—Synthesen, Produkte Und Moeglichkeiten Ihrs Einsatzes", Chemiker Zeitung, Huethig Verlag, Heidelberg, DE, vol. 96, No. 7, 1972, pp. 383-387.
Peit W.N.M. van Leeuwen and Carmen Claver: *Rhodium Catalyzed Hydroformylation*; ISBN 0-7923-6551-8 (2000); pp. 308-316.
Kurkin et al., Topchiev Institute of Petrochemical Synthesis, *Investigation of he Kinetic Relationships Governing the Hydroformylation of Isobutene*, Petroleum Chemistry, vol. 34, No. 5, pp. 393-398, 1994.
E. Billig and D.R. Bryant; Union Carbide Corporation; Kirk-Othmer: Encyclopedia of Chemical Technology, Fourth Edition, vol. 17, (1996), *Oxo Process*; pp. 902-919; p. 903 last two lines, referring to A.A. Oswald et al., A Presentation at the Lubrizol Award Symposium of the 1982 Spring ACS Meeting, Las Vegas.

* cited by examiner

*Primary Examiner* — Sudhakar Katakam
(74) *Attorney, Agent, or Firm* — Andrew B. Griffis; Leandro Arechederra, III (57) ABSTRACT

Mixed butene streams containing butene-1 and isobutylene and optionally butene-2 are hydroformylated under conditions that hydroformylates all the monomers to yield a mixture of valeraldehydes. Higher temperatures and/or longer residence times and/or higher partial pressure of carbon monoxide than in conventional processes are used to ensure hydroformylation of all the monomers.

14 Claims, 1 Drawing Sheet

Figure 1

HYDROFORMYLATION OF BUTENES COMPRISING ISOBUTYLENE

CROSS REFERENCE TO RELATED APPLICATIONS

This application is a national stage filing of International Patent Cooperation Treaty Application No. PCT/EP2004/010622 filed Sep. 17, 2004, the disclosure of which is fully incorporated herein by reference.

FIELD OF THE INVENTION

The present invention relates to saturated C5 aldehydes and their derivatives and in particular C5 aldehydes that are produced by the hydroformylation of butenes. The invention further relates to unsaturated aldehydes that may be obtained from the aldol condensation of such aldehydes, saturated aldehydes and unsaturated and saturated alcohols that may be obtained from hydrogenation of such unsaturated aldehydes, and carboxylic acids that may be obtained from oxidation of such saturated aldehydes. Furthermore the invention relates to the subsequent reaction and derivatives of such products, primarily esters.

BACKGROUND

The invention is particularly concerned with products and their derivatives obtained by the hydroformylation of C4 feeds comprising a mixture of isobutylene and at least one normal butene, and optionally other C4 components such as butane.

In this invention, the term butene or butylene generically refers to all hydrocarbon compounds having 4 carbons and at least one unsaturated bond that bonds together two carbons. Examples of specific butenes include, but are not limited to, butene-1, butene-2 (which refers to the combination of the cis and trans forms), isobutene or isobutylene, and butadiene. Thus, the generic term butene or butylene refers to the combination of all types of specific butene compounds.

Butene streams are used as raw materials for hydroformylation to produce valeraldehyde. In some commercial operations valeraldehyde is then dimerised and the product of dimerisation hydrogenated to produce 2 propyl heptanol or mixtures thereof with other alcohols which are finding use as alcohols in esterification reactions to produce plasticiser esters. Alternatively valeraldehyde may be hydrogenated to produce pentanol or amyl alcohol or mixtures of different isomers thereof which may be used as a solvent or in the production of materials such as zinc dialkyl dithiophosphates. The valeraldehyde may also be oxidised to produce valeric acid or isomer mixtures thereof which may be used in synthetic ester lubricant production.

Butenes have generally been obtained from $C_4$ cuts that are obtained from steam cracking and catalytic cracking refinery processes. These cuts typically contain a mixture of $C_4$ saturated and unsaturated materials including butadiene, normal butenes including both butene-1 and butene-2, of which both the cis- and the trans-form typically occur, and isobutylene. The butadiene may be removed by extraction or reaction, or converted by selective hydrogenation to produce a stream which contains predominantly normal butenes and isobutylene; such a stream is sometimes known as raffinate-1. The composition of such a stream in terms of the different hydrocarbon molecules may be determined by using conventional gas chromatographic techniques.

More recently butene streams have become available from an olefin stream obtained from an oxygenate conversion reaction. Such a butene stream is characterized by having a high butene content, but is low in components that can act as catalyst poisons. Although the butene components generally include a relatively high concentration of the more undesirable butene-2 and isobutylene compounds, we have found that the stream can be hydroformylated to convert a significantly high portion of those components to aldehyde products, which may then be further reacted in the manner described above.

Oxygenates used as feed to, or formed during, the oxygenate conversion to olefins process, can be present in the butene stream. Such components will not significantly affect the hydroformylation process, nor significantly affect the resulting aldehyde or aldehyde derivative products.

In one embodiment of this invention, the butene stream used in the invention is separated from an olefin stream that is obtained by contacting oxygenate with an olefin forming catalyst. The oxygenate comprises at least one organic compound containing at least one oxygen atom. Non-limiting examples include aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$-$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

U.S. Pat. Nos. 6,770,791 and 6,784,330 describe how butene feeds for use in this invention may be obtained by the conversion of an oxygenate.

It may be desirable to increase the ethylene yield in the oxygenate to olefin process, since ethylene is typically of greater commercial value than other olefins produced in the process. One way of increasing the ethylene yield in the oxygenate to olefin process is to operate the process such that there is less than 100% conversion of oxygenate to olefin product. This means that not all of the oxygenate feed will be completely converted to olefin or some other final non-water product. Less than 100% conversion can also mean that some of the oxygenate feed is not converted, or that not all intermediate products are completely converted to olefin. For example, dimethyl ether can be used as a feed or it may form as an intermediate product in the conversion to olefin. Therefore, the presence of dimethyl ether in the olefin product will generally imply that the conversion of oxygenate to olefin is less than 100%. By the same manner, other oxygenates, such as acetaldehyde, may be present, also indicating less than 100% conversion of feed or intermediate products.

In order to obtain the butene feeds from olefins produced from oxygenates for use in this invention, it is desirable to separate a butene rich stream from the olefin product stream produced in the oxygenate to olefin process. Although it is preferred to obtain a butene rich stream that is low in oxygenate concentration, this invention provides the advantage that a high degree of separation of non-butene compounds is not necessary. For example, propylene and pentene can be relatively easily removed from butene. Dimethyl ether, which may be present in the olefin product stream in rather large quantities at less than complete conversion, will tend to separate with the propylene rich stream. Although some oxygenate contaminants, particularly acetaldehyde, are likely to be present in the separated butylene stream, little if any oxygenate removal would be required to use the stream in further derivative processing if certain processes are used. According to this invention, it is desirable to use a rhodium hydroformylation catalyst for derivative processing of the separated butylene stream, because little to no pretreatment of the butylene stream for oxygenate removal would be required. Such catalyst is particularly suited to tolerate relatively high levels of acetaldehyde.

Separation can be accomplished using conventional means. Conventional distillation techniques are preferred.

It is known that within butene mixtures the different butene species have a different reactivity in hydroformylation reactions. For instance when using a rhodium catalyst in conjunction with a phosphine ligand such as triphenyl phosphine, butene-1 is considerably more reactive than butene-2 which has been more reactive than isobutylene. In addition it is known that the different pentanals produced by the hydroformylation of mixed butene feeds have different reactivities in subsequent aldolisation reactions with normal pentanal being considerably more reactive than 2-methyl butanal and accordingly various attempts have been made to keep the ratio of normal pentanal to 2-methyl butanal (sometimes known as the normal-to-iso ratio) as high as possible, such as is described in U.S. Pat. No. 4,426,542. 3 methyl butanal which is produced by the hydroformylation of isobutylene is however more reactive than 2 methyl butanal in aldol reactions but is difficult to produce from a butene mixture due to its lack of reactivity in rhodium catalysed hydroformylation.

During the hydroformylation of mixed butene feeds containing 1 butene and cis- and trans-2-butene, these materials will convert to a mixture of normal valeraldehyde and 2 methyl butyraldehyde. In order to enhance the reactivity and usefulness of the aldehyde it is desirable to increase the proportion of the normal valeraldehyde that is present, and when a rhodium catalyst is employed, this can be influenced by the choice of the ligand used in conjunction with the rhodium.

Isobutylene or isobutene is not considered to be generally reactive in rhodium catalysed hydroformylation and has generally been removed prior to hydroformylation. However when subject to hydroformylation, isobutylene is known to produce 3 methyl butyraldehyde at low conversion.

It is also known that mixed butene feeds containing isobutylene can be hydroformylated (including the hydroformylation of the isobutylene) by the use of a cobalt catalyst system. However such a system results in considerable isomerisation resulting in a high selectivity of normal butenes to the less desired 2-methyl butanal, and in hydrogenation resulting in the formation of considerable amounts of C5 alcohols which cannot then be used in subsequent aldolisation reactions.

U.S. Pat. No. 4,969,953 illustrates the hydroformylation of mixed butene feeds containing isobutylene using a rhodium catalyst in conjunction with a triphenyl phosphine ligand and states that the reaction speed of each component of butenes is different. Examples 1 and 2 use a feed containing 4% isobutylene, Example 1 achieves a 26% conversion of isobutylene resulting in a composition having a normal-to-iso ratio of 10 and a ratio of 3 methyl butanal to 2 methyl butanal of only 0.2; Example 2 employs higher pressures and obtains a higher conversion of both isobutylene and butene-2 to produce a pentanal mixture in which the ratio of 3 methyl butanal to 2 methyl butanal is again 0.2. Example 3 employs a mixed butene feed containing 51.5% isobutylene at the lower pressure and obtains a 2.3% conversion of isobutylene to produce a pentanal mixture containing 3 methyl-butanal and 2 methyl-butanal in a ratio of only 0.1.

U.S. Pat. No. 6,100,432 shows the separation of isobutylene from raffinate-1, producing a raffinate-2, prior to hydroformylation with a rhodium catalyst. U.S. Pat. No. 4,287,370 states that the $C_4$ feed to hydroformylation should contain no more than 1 wt % isobutylene. Similarly US Publication 2003/0022947 A1 discloses hydroformylation of raffinate-2, an isobutene depleted stream said to contain no more than 5 mol % isobutene. In this patent application, only the butene-1 is hydroformylated, the butene-2 and the isobutylene being substantially unreacted. An article by Walter J Scheidmeir of BASF in Chemiker-Zeitung 96 Jahrgang (1972) Nr 7. pp 383-387 shows the hydroformylation of a butene stream containing significant amounts of isobutylene (i.e. 46%) in which most of the unsaturated materials including the isobutylene, are converted. In this case, it is clear that cobalt salts were used as the hydroformylation catalyst, as evidenced by the high selectivity to alcohols in the product composition as well as the high yield of dimethylpropanal and dimethylpropanol that are reported, a combination of features that is typical for a high pressure cobalt based catalyst system, and atypical for the low pressure rhodium and phosphorus liganded catalyst systems. The product mix, excluding heavies, was reported to contain as much as 39.6%, presumably by weight, of various $C_5$ alcohol isomers, and respectively 1.2% and 4.1% of dimethylpropanal and dimethylpropanol. U.S. Pat. No. 6,555,716 describes a process in which raffinate-1 is fed to a hydroformylation reactor that employs a rhodium catalyst with a two phase aqueous system using a water soluble ligand, i.e. trisulphonated triphenylphosphine. However, far from all the isobutylene is converted, the highest conversion of isobutylene being 13.6% in Example 13. Furthermore the yield in this reaction is low and high catalyst recycle volumes are required, giving the process as described a low effectivity and a low efficiency.

SUMMARY

We have now found that C4 feeds, i.e. mixed butene feeds containing normal butene(s) and isobutylene may be hydroformylated to produce new C5 aldehyde mixtures with a high ratio of normal valeraldehyde to 2 methyl butyraldehyde and an increased ratio of 3 methyl butyraldehyde to 2 methyl butyraldehyde.

We have also found that the ratio of 3 methyl butanal to 2 methyl butanal may be increased by increasing the extent of hydroformylation of isobutylene in C4 (mixed butene) feeds and that a more reactive aldehyde mixture may be obtained. In addition the reactivity of the mixed valeraldehyde material may be increased by employing conditions that favour the conversion of cis- and trans-2 butene to normal valeraldehyde. This has the combined benefits that there is no need for isobutylene removal from conventional mixed butene feeds prior to hydroformylation and a more reactive C5 aldehyde mixture is obtained. Furthermore the more reactive C5 aldehyde mixture and its derivatives are novel and useful chemical compositions.

Accordingly the present invention provides a C5 aldehyde mixture comprising n-pentanal, 3-methyl-butanal and 2-methyl-butanal wherein
   i. the ratio of n-pentanal to 2-methyl-butanal is from 3:1 to 100:1 and
   ii. the ratio of 3-methyl-butanal to 2-methyl-butanal is at least 0.3:1.

In such C5 aldehyde mixture the ratio of 3-methyl-butanal to 2-methyl-butanal is preferably at least 0.5:1, more preferably at least 1:1, yet more preferably at least 10:1 and most preferably at least 20:1. For example the ratio is preferably in the range 0:3:1-30:1, more preferably 0.5:1-25:1 and most preferably 1:1-20:1. The ratio of n-pentanal to 2-methyl-butanal is preferably in the range 5:1-50:1, more preferably 8:1-40:1, yet more preferably 10:1-35:1 such as 15:1-35:1, and most preferably 20:1-30:1.

In a further embodiment the invention provides a process for the production of an aldehyde mixture comprising hydroformylating a C4 feed containing one or more normal butenes and from 15 wt % to 50 wt % isobutylene in a single liquid phase in the presence of a catalyst comprising a rhodium complex in conjunction with an organophosphorus ligand (preferably comprising a tertiary organophosphine or an organophosphite) and under conditions that convert normal butenes and converts at least 15% of the isobutylene to produce a mixture of isomers of valeraldehyde.

In a yet further embodiment the invention provides a process for the production of an aldehyde mixture comprising hydroformylating a C4 feed containing one or more normal butenes and from 2 wt % to 50 wt % isobutylene in a single liquid phase in the presence of a catalyst comprising a rhodium complex in conjunction with an organophosphorus ligand comprising an organophosphite and under conditions that convert normal butenes and convert at least 15% of the isobutylene to produce a mixture of isomers of valeraldehyde.

In both process embodiments we prefer that at least 20% or 30%, more preferably at least 45%, even more preferably at least 55%, and most preferably at least 60% of the isobutylene is converted.

The invention also provides for aldehyde products containing mixtures of various valeraldehydes. In one embodiment, there is provided an aldehyde mixture comprising at least 85 wt % n-valeraldehyde, based on total amount of aldehydes in the mixture. Preferably, the aldehyde mixture comprises at least 88 wt % n-valeraldehyde, more preferably at least 90 wt % n-valeraldehyde, and most preferably at least 92 wt % n-valeraldehyde, based on total amount of aldehydes in the mixture.

The mixture will generally include a limited quantity of 3-methylbutanal. In one embodiment, the mixture is comprised of not greater than 8 wt % 3-methylbutanal, based on total amount of aldehydes in the mixture. Preferably, the mixture is comprised of not greater than 6 wt % 3-methylbutanal, more preferably not greater than 5 wt % 3-methylbutanal, and most preferably not greater than 4 wt % 3-methylbutanal, based on total amount of aldehydes in the mixture.

Although the amount of 3-methylbutanal in the aldehyde mixture is relatively low, there will generally be at least an easily measurable amount present. In one embodiment, the mixture is comprised of at least 1 wt % 3-methylbutanal, based on total amount of aldehydes in the mixture. In another embodiment, the mixture is comprised of at least 2 wt % 3-methylbutanal, or at least 3 wt % 3-methylbutanal, based on total amount of aldehydes in the mixture.

The mixture will also generally include a limited amount of 2-methylbutanal. In one embodiment, the mixture is comprised of not greater than 7 wt % 2-methylbutanal, based on total amount of aldehydes in the mixture. Preferably, the mixture is comprised of not greater than 6 wt % 2-methylbutanal, more preferably not greater than 5 wt % 2-methylbutanal, and most preferably not greater than 2 wt % 3-methylbutanal, based on total amount of aldehydes in the mixture.

Although the amount of 2-methylbutanal in the aldehyde mixture is also relatively low, there will generally be at least an easily measurable amount present. In one embodiment, the mixture is comprised of at least 0.05 wt % 2-methylbutanal, based on total amount of aldehydes in the mixture. In another embodiment, the mixture is comprised of at least 0.1 wt % 2-methylbutanal, based on total amount of aldehydes in the mixture.

The C4 feed, ie butene stream, used in the process of this invention may be obtained from the cracking of hydrocarbon gases, condensates or petroleum feedstocks or from oxygenate conversion. The stream preferably contains at least about 60 wt % butenes, based on total weight of the stream. Streams more concentrated in butene compounds are still more desirable. For example, butene streams containing at least about 70 wt %, 80 wt %, and 90 wt % total butenes, based on total weight of the butene stream, are progressively more desirable.

Of the total amount of butenes present in the butene feed stream, there is desirably a significant concentration of butene-1. However, when the butene feed streams are predominantly recovered from olefin product streams of oxygenate conversion reactions, such streams may include a significant amount of butene-2, and to a lesser extent, a significant amount of isobutene. Although butene-1 is more readily converted to aldehyde via hydroformylation reactions, this invention provides for significant conversion of butene-2, as well as isobutene, to aldehyde via hydroformylation.

In one embodiment, of the total amount of butenes present in the butene feed stream, at least 10 wt % of the total butene concentration is butene-1. Preferably at least 15 wt %, and more preferably 20 wt %, based on total weight of butene present in the stream, is butene-1. The concentration of butene-1 is generally limited in this invention to not greater than about 50 wt %, based on total weight of butene in the stream. In some cases, the butene stream contains not greater than about 40 wt % or 30 wt % butene-1, based on total weight of butene in the stream. Thus, in various embodiments, the butene stream can comprise from 10 wt % to 50 wt % or 15 wt % to 40 wt % or 20 wt % to 30 wt % butene-1, based on total weight of butene in the butene stream.

In one embodiment, of the total amount of butenes present in the butene feed stream used in this invention, at least 40 wt % of the total butene concentration is butene-2 (the combined cis and trans forms). In other embodiments, at least 50 wt %, or 60 wt %, based on total weight of butene present in the stream, is butene-2. The concentration of butene-2 is generally limited to not greater than about 80 wt %, based on total weight of butene in the stream. Preferably, the butene stream contains not greater than about 75 wt %, and more preferably not greater than about 70 wt % butene-2, based on total weight of butene in the stream. Thus, in various embodiments, the butene stream can comprise from 40 wt % to 80 wt % or 50 wt % to 75 wt % or 60 wt % to 70 wt % butene-2, based on total weight of butene in the butene stream.

In one embodiment, of the total amount of butenes present in the butene stream used in this invention, at least 2 wt % of the total butene concentration is isobutylene, particularly when the butene feed is obtained from oxygenates. In other embodiments, at least 3 wt %, or 4 wt %, based on total weight of butene present in the stream, is isobutylene. Where butenes obtained from oxygenates are used, the concentration of isobutylene is generally limited in this invention to not greater than about 15 wt %, based on total weight of butene in the stream. When a butene stream obtained by the conversion of oxygenates is used, the butene stream contains typically not greater than about 12 wt %, and more typically not greater than about 8 wt % isobutylene, based on total weight of butene in the stream. Thus, in various embodiments, the butene stream can comprise from 2 wt % to 15 wt % or 3 wt % to 12 wt % or 4 wt % to 8 wt % isobutylene, based on total weight of butene in the butene stream.

It is also desirable that the butene containing feed stream be separated so as to contain a lesser amount of propylene. Preferably a butene containing feed stream should contain less than about 0.5 wt % propylene, based on total weight of the butene stream. Streams containing even lesser amounts of propylene are preferred. For example, butene streams containing not greater than about 0.3 wt % propylene, not greater than about 0.1 wt % propylene, and not greater than about 0.05 wt % propylene, based on total weight of the butene stream, are progressively more preferred.

It is also desirable that the butene containing feed stream be separated so as to contain a lesser amount of total pentenes. Preferably a butene containing feed stream should contain less than about 0.5 wt % total pentenes, based on total weight of the butene stream. Streams containing even lesser amounts of total pentenes are preferred. For example, butene streams containing not greater than about 0.3 wt % total pentenes, not greater than about 0.1 wt % total pentenes, and not greater than about 0.05 wt % total pentenes, based on total weight of the butene stream, are progressively more preferred.

A butene stream separated and recovered from the olefin product of an oxygenate conversion process requires little if any treatment to remove contaminants. For example, little if any treatment is needed to remove compounds containing sulfur, nitrogen and chlorine, which can act as poisons to hydroformylation catalysts. In certain cases, however, it may also be appropriate to mildly hydrogenate the butene stream to remove dienes or acetylenes, which can be present in the butene stream, and which can act as temporary inhibitors to the hydroformylation catalysts that only slowly hydrogenate to the corresponding olefins.

Butenes obtained by cracking hydrocarbon streams can also be used in this invention. Butenes obtained from such a source can also be combined with butenes obtained from an oxygenate conversion reaction. This is because the butenes obtained by a cracking process are generally high in non-reactive hydrocarbon components such as alkanes, are high in branchiness, and are high in other undesirable by-products such as sulfur, nitrogen and/or chlorine. Therefore, additional purification of a butene stream containing butenes obtained from a cracking process may be needed.

Conventional processes can be used for removing undesirable components from the olefin feed stream of this invention. Such methods include water washing, caustic scrubbing, distillation, and fixed bed adsorption. Other desirable methods, such as those found in Kirk-Othmer Encyclopedia of Chemical Technology, 4th edition, Volume 9, John Wiley & Sons, 1996, pg. 894-899, the description of which is incorporated herein by reference, can also be used. In addition, purification systems such as that found in Kirk-Othmer Encyclopedia of Chemical Technology, 4th edition, Volume 20, John Wiley & Sons, 1996, pg. 249-271, the description of which is also incorporated herein by reference, can be used.

The C4 feed (butene stream) used in this invention preferably has a low sulfur and/or nitrogen and/or chlorine content. According to one embodiment, the butene stream also contains acetaldehyde at a concentration that does not substantially adversely affect the catalytic activity of the hydroformylation catalyst.

The sulfur content of the butene feed used in this invention should be sufficiently low such that the activity of the catalyst used to form the hydroformylated product is not substantially inhibited. Preferably, the sulfur content in the butene feed is not greater than about 10 ppm; more preferably, not greater than about 5 ppm; and most preferably, not greater than about 2 ppm by weight, calculated on an atomic basis. Most preferably the feed contains below 50 ppb of sulphur and even more preferably less than 20 or even less than 10 ppb by weight of sulfur.

The nitrogen content, in particular organic nitrogen compounds such as cyanides, of the butene feed used in this invention should also be sufficiently low such that the catalytic activity of the catalyst used to form the hydroformylated product is not substantially inhibited. Preferably, the nitrogen content in the olefin feed is not greater than about 10 ppm; more preferably, not greater than about 5 ppm; and most preferably, not greater than about 2 ppm by weight, calculated on an atomic basis. Most preferably the feed contains below 50 ppb of nitrogen and even more preferably less than 20 or even less than 10 ppb by weight of nitrogen.

The chlorine content, in particular ionic chlorine, of the butene feed used in this invention should also be sufficiently low such that the catalytic activity of the catalyst used to form the hydroformylated product is not substantially inhibited. Preferably, the chlorine content in the olefin feed is not greater than about 5 ppm; more preferably, not greater than about 2 ppm; and most preferably, not greater than about 1 ppm by weight, calculated on an atomic basis. Most preferably the feed contains below 50 ppb of chlorine and even more preferably less than 20 or even less than 10 ppb by weight of chlorine.

The butene stream can contain a non-toxic amount of acetaldehyde, particularly if the butene stream is obtained from the olefin product of an oxygenate to olefin conversion reaction. This means that acetaldehyde will be present in the stream, which provides the advantage that treatment or removal is not necessary. However, excessive quantities are not desirable from a practical standpoint that reactor volume is inefficiently utilized. A butene stream containing up to about 5000 ppm by weight, based on total weight of the butene stream, is highly acceptable. The lower the quantity of acetaldehyde, the greater the desirability from a hydroformylation operation standpoint. However, lower quantities of acetaldehyde may mean that at least some removal process has been performed. The presence of acetaldehyde at levels of about 4000 ppm by weight, about 3000 ppm by weight, about 2000 ppm by weight, about 1000 ppm by weight, about 500 ppm by weight, about 250 ppm by weight, about 100 ppm by weight, based on total weight of the butene stream, are considered acceptable.

A variety of hydroformylation catalysts can be used in this invention. Rhodium catalysts are preferred. Rhodium catalysts containing an organophosphorus ligand are particularly preferred. Hydroformylation reactions of lower olefins such as ethylene, propylene and butenes have generally employed rhodium catalyst stabilised by phosphorus containing ligands operated in what is known as the low pressure oxo (LPO) technology originally developed by Union Carbide Corporation and currently available under license from Davy Process Technology. In another hydroformylation technology, cobalt containing catalysts are used and the process is operated at higher pressures. In a similar way to cobalt, also rhodium catalysed hydroformylation may be operated at higher pressures, without a stabilizing ligand other than carbon monoxide or with a weak ligand like e.g. triphenylphosphine oxide (TPPO).

As previously mentioned isobutylene has been considered to be an inert in the low pressure, rhodium catalysed hydroformylation processes that are offered for license, primarily by Union Carbide Company (now Dow Chemical Company) and Davy Process Technology (DPT). Older versions of this technology use triphenylphosphine (TPP) as the ligand for the rhodium catalyst. This ligand forms rather strong complexing bonds with the rhodium metal, which is noticed by a significant reduction of activity as compared to hydroformylation using rhodium without the TPP ligand. In order to obtain a high selectivity to the normal aldehyde product, preferred over its 2-methyl branched equivalent, they also typically use a high phosphorus to rhodium ratio which leads to even more reduced reaction rates. In order to be economical, the process is therefore operated at a rather low per pass conversion combined with the use of significant recycles, which make inerts, such as isobutylene, in the feeds very undesirable. A newer version of this technology uses a bis-phosphite ligand. Its complexing bonds are less strong, yet its selectivity to the normal aldehyde product is even higher than with TPP. This allows the use of a lower phosphorus to rhodium ratio, such that these catalysts are more reactive and therefore can run once-through at acceptable conversions, and the process can use reactors in series. The branched product structure of isobutylene has however also been considered undesirable with this catalyst, and therefore the isobutylene is preferentially removed from the feed, so that typically raffinate-2 is also proposed as the preferred feedstock for low pressure hydroformylation, using the bis-phosphite version technology.

Accordingly when using rhodium based low pressure oxo technology with raffinate-1, it has been common practice to separate the isobutylene from the normal butenes in the raffinate-1 to produce a stream containing only n-butenes which can be used for hydroformylation; such a stream is sometimes known as raffinate-2. The separation of isobutylene from raffinate-1 is however not an easy process and is expensive and energy consuming. If fractionation is used, a mixture of butene-1 and isobutene tends to be obtained overhead, whilst the butene-2 tends to be obtained at the bottom of the fractionation tower. Clearly this is not beneficial if one wants to obtain a butene-1 stream that is substantially free of isobutylene. Accordingly superfractionation may be used; however, this has very high energy requirements and is expensive to operate and complex to design. Furthermore, even the use of superfractionation may not result in complete separation of the isobutylene.

We have found that by increasing temperature and/or the partial pressure of carbon monoxide in the low pressure hydroformylation reaction employing a single, non aqueous liquid phase reaction, isobutylene can be made to react when using the traditional rhodium based phosphorus liganded catalyst systems. Because the hydroformylation rate is proportional to the $H_2$ to CO ratio used in the reactor, it is also preferable to increase the $H_2$ partial pressure as well as the carbon monoxide partial pressure. Consequently, the present invention in one of its embodiments requires a higher operating pressure, not foreseen in a typical single liquid phase low pressure rhodium based hydroformylation process design.

The operation of this process avoids the need for the complicated and expensive separation of isobutylene from the unsaturated $C_4$ feed such as raffinate-1.

The $C_4$ streams that are used in the present invention and that contain more than 2 wt % isobutylene may be obtained from the conversion of oxygenates to olefins as described above. The preferred feeds contain more than 15 wt % isobutylene and are conveniently those obtained in the steam cracking or catalytic cracking of hydrocarbon gases, condensates and/or petroleum feedstocks. The composition of the streams will depend upon the composition of the petroleum feedstock and the conditions employed in the steam cracking or catalytic cracking operation. Typically such feeds contain from 15 to 50 wt % isobutylene and from 40 to 85 wt % normal butenes, any remainder being primarily n-butane and isobutane. More typically the feeds contain from 18 to 45 wt % isobutylene. The normal butenes are generally a mixture of butene-1 and butene-2 (cis- and trans-form) and the relative proportions of those materials will also depend upon the composition of the petroleum feed and the conditions employed in the steam cracking or catalytic cracking operation and in the subsequent process steps. This is because isomerisation of the double bond of the n-butene readily occurs under many process conditions, so butene-1 easily converts to butene-2 and vice-versa. A preferred feed however contains from 12% to 30% of butene-1 and from 17% to 40% of butene-2. Other materials such as $C_3$ and $C_5$ hydrocarbons and trace quantities of butadienes, $C_4$-acetylenes may be present in the $C_4$ stream.

In particular the $C_4$ stream from cracking may contain components that are poisons to the rhodium catalyst or which inhibit the hydroformylation reaction, examples being certain sulphur or chlorine species. To the extent that their presence is undesired, they may be removed or their content reduced by techniques known in the art.

The preferred hydroformylation conditions that are employed convert all the butenes during the hydroformylation reaction; typically above 80% of the butene-1 is converted and above 50% of the isobutylene and of the butene-2s are converted. We prefer to use rhodium catalysed hydroformylation at low pressures but have found that in order to hydroformylate the isobutylene, higher temperatures and/or longer residence times and/or higher partial pressure of carbon monoxide are advantageously used. However, it is desirable to maintain the hydrogen to carbon monoxide ratio up during the hydroformylation and so it may be necessary to increase the hydrogen partial pressure also and accordingly a higher overall pressure may be used.

The butene hydroformylation is preferably carried out in the presence of a catalyst comprising a rhodium complex in conjunction with an organophosphorus ligand. This organophosphorus ligand may be a tertiary organophosphine or an organophosphite. The process employing TPP or other phosphines is typically operated at conditions (high phosphorus to rhodium ratio (P/Rh) and low partial pressure of carbon monoxide ($p_{CO}$) where almost only butene-1 reacts, due to the desire to produce a valeraldehyde mixture having a high normal to iso ratio (n/i or n/iso), favouring the production of n-valeraldehyde vs 2-methylbutanal. The triorganophosphine ligand can be for example a trialkylphosphine such as tributylphosphine, a $C_1$-$C_6$ alkyldiarylphosphine such as butyldiphenylphosphine, an aryldialkylphosphine such as phenyldibutylphosphine, an aryldialkyl diphosphine such as cyclohexyldiphenyl phosphine, tetraphenyldiphosphinomethane, 1,2-bis(diphenyl phosphino) ethane, 1,3-bis(diphenyl phosphino) propane, 1,4-bis(diphenyl phosphino) butane, and the bisphosphine ligands described in EP-A 279,018, EP-A 311,619, WO 90/06810 and EP-A 71,281. However particular phosphines such as triphenylphosphine, tri-p-tolylphosphine, trinaphthylphosphine, phenyldinaphthylphosphine, diphenylnaphthylphosphine, tri(p-methoxyphenyl)phosphine, tri(p-cyanophenyl)phosphine, tri(p-nitrophenyl)phosphine, p-N,N-dimethylaminophenylbisphenylphosphine and the like are preferred. Triphenylphosphine (TPP) is most preferred.

Organophosphite ligands can be those disclosed in U.S. Pat. No. 4,599,206, U.S. Pat. No. 4,668,651, U.S. Pat. No. 4,737,588, U.S. Pat. No. 4,748,261, U.S. Pat. No. 4,769,498, U.S. Pat. No. 4,774,361, U.S. Pat. No. 4,789,753, U.S. Pat. No. 4,835,299, U.S. Pat. No. 4,871,880, U.S. Pat. No. 4,885,401, U.S. Pat. No. 5,179,055, U.S. Pat. No. 5,288,918, U.S. Pat. No. 5,312,996, U.S. Pat. No. 5,364,950, U.S. Pat. No. 5,681,473, U.S. Pat. No. 5,756,855, WO 97/20793. Preferred is 6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin, or 6,6'-[[3,3',5,5'-tetrakis(1,1-dimethylpropyl)-1,1'-biphenyl]-2,2'-diyl]bis(oxy)]bis-dibenzo[d,f][1,3,2]-dioxaphosphepin, or 6,6'-[[3,3'-bis(1,1-dimethylethyl)-5,5'-dimethoxy[1,1'-biphenyl]-2,2'-diyl]bis(oxy)]bis-dibenzo[d,f][1,3,2]-dioxaphosphepin, or tris(2,4,6-di-t-butylphenyl)-phosphite. Most preferred is 6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin. Ionic varieties of such phosphites are disclosed in U.S. Pat. No. 5,059,710 and U.S. Pat. No. 5,113,022.

The hydroformylation process may generally be carried out in a manner known by the persons skilled in the art, for example by the process according to U.S. Pat. No. 4,247,486, U.S. Pat. No. 4,287,370, U.S. Pat. No. 5,053,551, U.S. Pat. No. 6,100,432, WO 02/00582, DE 10128325 although with some of them, higher temperatures and/or longer residence times and/or carbon monoxide partial pressures will be used.

The catalysts employed in the low pressure oxo hydroformylation reactions are typically rhodium based catalyst that are stabilised by a ligand. Since the advent of rhodium low pressure oxo technology there has been a continuing evolution of the ligands. The most frequently used ligands have been triphenylphosphinic, such as discussed above. Those catalysts employing these ligands would convert primarily butene-1. Accordingly to date, the hydroformylation cycle using rhodium catalyst with such ligands and an isobutylene containing feed involves:
a) removal of the isobutylene from the feed
b) subjecting the normal butenes to hydroformylation wherein only butene-1 would be converted to valeraldehyde and/or pentanol.
c) separation of the unreacted butene-2 from the valeraldehyde and/or pentanol.

The present invention changes this process in that the isobutylene is converted to useful product during the hydroformylation reaction.

More recently bisphosphite ligands, e.g. of the formula

Ligand A have been developed and these are described in U.S. Pat. No. 5,364,950, U.S. Pat. No. 4,835,299 and U.S. Pat. No. 5,288,918. We prefer to use the catalysts employing those ligands in the hydroformylation of $C_4$ feeds containing normal butenes and isobutylene, with high conversion substantially of all the unsaturated $C_4$ materials to useful valeraldehyde. These ligands are capable of converting significant portions of all three butenes. Use of these catalysts allows relatively low P/Rh ratios while maintaining desired product selectivity.

Accordingly the hydroformylation cycle using these phosphite ligands comprises subjecting a mixed $C_4$ olefin feed containing isobutylene to hydroformylation under conditions that react substantially all the unsaturated $C_4$ materials to produce valeraldehyde.

During the hydroformylation reaction it is believed that the carbon monoxide competes with the phosphorus compound to co-ordinate as ligands to the rhodium metal. Accordingly a higher carbon monoxide partial pressure will co-ordinate more carbon monoxide with the rhodium and less of the much more bulky phosphorus containing ligand will co-ordinate. In this way the metal in the complex becomes more accessible for olefin bonds that are more substituted, like internal olefins and/or branched olefins, such as isobutylene. Accordingly by increasing the partial pressure of the carbon monoxide, isobutylene can be made to hydroformylate at acceptable rates, especially with the bis-phosphite ligand system, but also with the older rhodium/triphenyl phosphine catalyst system. An additional effect of the higher partial pressures of carbon monoxide is a higher resistance of the rhodium complex against the formation of rhodium clusters, which become less and less active hydroformylation catalysts as more rhodium atoms tie up together, and ultimately may come out of solution and form precipitates. As this deactivation process goes faster at higher temperatures, the higher partial pressures of carbon monoxide permit the operation of the process at higher temperatures, and hence bring even greater additional benefits in terms of reaction rate, which can be translated into productivity, yield and/or investment benefits, or a combination thereof, as the practitioner may like.

As an extension the valeraldehyde produced by this invention may then be converted to 2-propyl heptanol or mixtures containing 2-propyl heptanol by dimerisation, usually by an aldol reaction, and hydrogenation.

According to the invention therefore, hydroformylation may be accomplished using phosphite ligands with careful control of the temperatures, residence times and partial pressures of the reactants and/or products. Thus, when a triorganophosphine ligand is used, it is preferably used in an amount of at least 100 mol per gram atom of rhodium. Contrarily, if one prefers to forego the high selectivity to the normal aldehyde, one may use amounts of triorganosphosphine ligand that are much lower, like 40 or less mole per gram atom of rhodium, but also 20 or less, and even 10 or less, down to 5 or less, or even 2 or less, should one desire to do so. The residence time required for the target conversions is suitably adapted according to the activity of the chosen ligand and the P/Rh ratio. Preferably with bis-phosphite ligands the amount of ligand present is from 1 to about 40 moles of bisphosphite ligand per mole of rhodium, more preferably from 1 to 4 moles of bisphosphite ligand per mole of rhodium, said amount of ligand being the sum of both the amount of ligand that is bound (complexed) to the rhodium metal and the amount of free (non-complexed) ligand present. If desired, make-up ligand can be supplied to the reaction medium of the process at any time and in any suitable manner, e.g. to maintain a predetermined level of free ligand in the reaction medium. The temperature is generally in the range of 50 to 180° C., preferably in the range from 80 to 155° C., more preferably in the range from 85 to 135° C., even more preferably from 85 to 115° C. The total pressure is preferably not more than 10000 kPa. The partial pressure of carbon monoxide is preferably kept above 200 kPa but below 5000 kPa; and that of hydrogen is preferably kept in the range from 100 to 7000 kPa. We have found that when using a phosphite ligand such as Ligand A at a reaction temperature of 95° C. and a partial pressure of carbon monoxide of about 5 bar, a residence time of greater than 15 minutes results in a significant conversion of isobutylene.

When a phosphine ligand is used the preferred hydroformylation conditions are a total gas pressure (of hydrogen, carbon monoxide and olefinic unsaturated starting compound) of the hydroformylation process ranging from about 1 to about 30,000 kPa. In general, however, it is preferred that the process be operated at a carbon monoxide partial pressure of at least 0.2 MPa, more preferably at least 0.5 MPa as compared to the conventional technology which prefers and employs a carbon monoxide partial pressure of below 0.2 MPa. More preferably the carbon monoxide partial pressure is at least 1 MPa, better even 2.5 MPa or above, or 3.0 MPa or above. The total gas pressure of hydrogen, carbon monoxide and olefinic unsaturated starting compound is preferably more than about 1500 kPa and more preferably more than about 5000 kPa. The minimum total pressure is limited predominantly by the amount of reactants necessary to obtain a desired rate of reaction. In general $H_2$ to CO molar ratio of gaseous hydrogen to carbon monoxide may range from about 1:10 to 100:1 or higher, the more preferred hydrogen to carbon monoxide molar ratio being from about 1:1 to about 10:1. Further, the hydroformylation process may be conducted at a reaction temperature from about 45° C. to about 180° C., desirably in the range 50 to 180° C. In general a hydroformylation reaction temperature of about 50° C. to about 170° C. is employed for all types of olefinic starting materials, the more preferred reaction temperatures being from about 80° C. to about 160° C. particularly 80 to 155° C. especially 85 to 115° C. and most preferably from about 100, 110, 120, 130 or 140° C. upwards. We have found that when using the triphenylphosphine ligand at 110° C. and a carbon monoxide partial pressure of about 5 bar, a residence time of at least two and a half hours, generally at least three hours is required to hydroformylate the isobutylene. It is expected that this residence time may be further shortened as the concentration of the starting olefin is increased, and as the partial pressure of carbon monoxide and/or the temperature is further increased.

Any of these processes may use any suitable solvent. In general, it is preferred to employ as solvents one or more valeraldehydes and/or their liquid condensation by-products that are produced in situ during the hydroformylation process. Rhodium concentrations in the hydroformylation reaction medium may be, for example, in the range from about 10 ppm to about 1000 ppm, calculated as free rhodium. It is generally preferred to operate with from about 10 to 500 ppm of rhodium, and more preferably from 25 to 350 ppm of rhodium.

Using a rhodium hydroformylation catalyst, isobutylene will make primarily only one product, 3-methyl-butyraldehyde (also called 3-methyl-butanal or isovaleraldehyde or isopentyl aldehyde), and little to no 2,2-dimethyl-propionaldehyde is formed. This 3-methyl-butyraldehyde boils at 92.5° C., and is thus in practical terms inseparable by distillation from 2-methyl-butyraldehyde, which boils at 92.0° C. Both can (together) be distilled off from n-valeraldehyde, boiling at 103° C. (all at 1 atm). N-valeraldehyde and 2-methyl-butyraldehyde are the products of n-butene hydroformylation, and due to the higher oxonation rate of these n-butenes, are expected to be present in the product from the low pressure hydroformylation of raffinate-1. As alcohols these two monomethyl branched isomers remain difficult to separate, although their boiling points are further apart (131.4° C. for 3-methyl and 128° C. for 2-methyl butanol). As acids, the boiling points are again very similar (176.5° C. (3-Me) vs 177° C. (2-Me)). Although the two isomers may show different reactivities in several of the derivatisation reactions, most technical end-uses are not expected to be very sensitive to the location of the methyl branch on the alkyl chain, and the mixed product of this invention should be useful in the manufacture of alcohols for solvents, plasticisers, esters, xanthogenates, ZDDP; acids for esters as solvents, softeners, perfumes, synlubes, synlube additives. Other derivatives may be isomer sensitive, like alcohols for dehydration to isoprene (2-Me) and isoleucine, pinacol or pinacolone into pesticides or butizides in pharmaceuticals, or acids into fungicides, rodenticides, sedatives, narcotics and other drugs in which case separation of the isomers will be required at some step in the production process.

The invention has the benefit that a larger amount of valeraldehyde is obtained and in an extension of the present invention the valeraldehyde isomer mixture, as produced or a fraction thereof obtained by purification, is converted into 2 propyl heptanol or mixtures thereof with other alcohols preferably by aldol condensation followed by hydrogenation. In another extension the valeraldehyde or valeraldehyde mixture is hydrogenated to pentanol or pentanol mixtures or oxidised to pentanoic acid or mixtures of pentanoic acids.

The invention therefore provides a substantial improvement in the overall conversion and utilisation of $C_4$ refining streams avoiding the need for hitherto expensive and complex techniques for the separation of isobutylene from the $C_4$ refinery stream.

Butene hydroformylation has traditionally only been considered on raffinate-2 streams, from which isobutylene has been removed down to 1% wt or below, because of the higher upgrade achieved when converted to MtBE, EtBE, Butyl rubber, DIB/TIB or PIB. The current concept is to hydroformylate the streams with the isobutylene in them. Characteristic is the presence of 3-methyl-butanal, and also the low level of alcohols. Other $C_5$ aldehydes possible are n-valeraldehyde and 2-methyl-butanal. 2,2-dimethyl-propanal, if present, will be low due to the use of rhodium metal. Cobalt will give higher alcohol levels and higher presence of 2,2-dimethylpropanal/ol. The level of 3-methyl-butanal in this $C_5$ aldehyde mix depends on the choice of butene feedstock (level of isobutylene vs other butenes) and the choice of low pressure hydroformylation technology (conversion of the isobutylene vs the other butenes).

Isobutylene containing $C_4$ olefinic streams vary depending on their source and treatment. Table 1 shows some typical compositions.

TABLE 1

| | C4 feeds containing isobutylene | | | |
|---|---|---|---|---|
| | | Steamcracker Crude C4's | | MTO |
| Typical comp. Wt % | FCC C4 cut | After BD extraction | After Sel. Hydro | After Sel. Hydro |
| Stream ID | F1 | F2 | F3 | F4 |
| Isobutylene | 22 | 47 | 29 | 4 |
| Butene-1 | 14 | 25 | 29 | 21-24 |

TABLE 1-continued

C4 feeds containing isobutylene

| Typical comp. Wt % | FCC C4 cut | Steamcracker Crude C4's | | MTO |
|---|---|---|---|---|
| | | After BD extraction | After Sel. Hydro | After Sel. Hydro |
| Butene-2 cis | 12 | 8 | 10 | 27 |
| Butene-2 trans | 17 | 10 | 24 | 40-41 |
| n-Butane | 7 | 8 | 7 | 4-8 |
| Isobutane | 24 | 1 | 1 | .3 |
| | 96 | 99 | 100 | 100 |
| Remainder | C3-5s, BD | BD | — | |

FCC = Fluid Catalytic Cracking
BD = Butadiene
MTO = Methanol (or other oxygenates) To Olefins
Sel. Hydro = Selective Hydrogenation The $C_5$ aldehyde product mixtures obtained by the hydroformylation of such streams vary according to the composition of the feed and the hydroformylation technology deployed on them.

The amount of 3-methyl-butanal in the product mix will also depend on the conversion of isobutylene vs the other butenes, which one may be able to influence by ligand selection, by temperature, by residence time and by partial pressure of CO ($p_{CO}$) in the reactor. The order of reactivity of the butenes is typically butene-1>butene-2 (cis/trans)>isobutylene.

Higher $p_{CO}$ will tend to shift the ligand equilibrium to complexes that are more accessible by branched (and internal) olefins. So, it is expected that also Rh/phosphine technology may be made suitable for isobutylene conversion provided that the $p_{CO}$ can be raised.

The following $C_5$ aldehyde mixtures are predicted from the feeds described in Table 1 using the two ligand families discussed:

TABLE 2

$C_5$ aldehyde product mixes

| | Ligand family | | | | | | | |
|---|---|---|---|---|---|---|---|---|
| | Phosphines | | | | Phosphites | | | |
| % Conversion of | | | | | | | | |
| Butene-1 | 85 | | | | 99 | | | |
| Butene-2 | 43 | | | | 63 | | | |
| Isobutylene | 17 | | | | 48 | | | |
| N/iso (on n-C4s) | 10 | | | | 30 | | | |
| Feed stream ID | F1 | F2 | F3 | F4 | F1 | F2 | F3 | F4 |
| n-Valeraldehyde | 78 | 71 | 80 | 93-94 | 73 | 59 | 76 | 94 |
| 2-Me-butanal | 8 | 7 | 8 | 3 | 2 | 2 | 2 | 3 |
| 3-Me-butanal | 14 | 22 | 12 | 3-4 | 25 | 39 | 22 | 3 |
| 2,2-diMe-propanal | — | — | — | — | — | — | — | — |

The traditional hydroformylation of raffinate-2 feed (1% wt isobutylene), irrespective of its source—steamcracker or FCC, will inevitably give less than 1% wt 3-Me-butanal in the $C_5$ aldehyde mix.

The product of the hydroformylation reaction will generally require additional purification. Rhodium catalysed hydroformylation is employed and typically the reaction products are taken from the reactor as vapour and then condensed, although in some systems they can also be taken off as liquid which is subjected to a subsequent flash. The vapours obtained are then split into the paraffins, the aldehydes, the remaining olefins, unreacted feeds including carbon monoxide and hydrogen which can be recycled, and the heavies. Optionally also a portion of the remaining olefins, possibly containing also some paraffins, may be recycled.

The above $C_5$ aldehyde streams may be hydrogenated to alcohols or oxidised to acids using standard technology to produce mixtures with the same isomer backbone compositions, and which have some commercial relevance.

The composition of the alcohols and acids produced is set out in Table 3.

TABLE 3

$C_5$ alcohol and acid product mixes

| | Ligand family | | | | | | | |
|---|---|---|---|---|---|---|---|---|
| | Phosphines | | | | Phosphites | | | |
| | Feed stream ID | | | | | | | |
| | F1 | F2 | F3 | F4 | F1 | F2 | F3 | F4 |
| Alcohol product: | | | | | | | | |
| n-Amyl alcohol | 78 | 71 | 80 | 93-94 | 73 | 59 | 76 | 94 |
| 2-Me-butanol | 8 | 7 | 8 | 3 | 2 | 2 | 2 | 3 |
| 3-Me-butanol | 14 | 22 | 12 | 3-4 | 25 | 39 | 22 | 3 |
| 2,2-diMe-propanol | — | — | — | — | — | — | — | — |
| Acid product: | | | | | | | | |
| n-Valeric acid | 78 | 71 | 80 | 93-94 | 73 | 59 | 76 | 94 |
| 2-Me-butanoic | 8 | 7 | 8 | 3 | 2 | 2 | 2 | 3 |
| 3-Me-butanoic | 14 | 22 | 12 | 3-4 | 25 | 39 | 22 | 3 |
| 2,2-diMe-propanoic | — | — | — | — | — | — | — | — |

Accordingly the present invention further provides a $C_5$ alcohol mixture consisting essentially of normal and mono-methyl branched alcohols and comprising n-pentanol, 2-methyl-butanol and 3-methyl-butanol wherein
  i. n-pentanol and 2-methyl-butanol are present in a ratio from 3:1 to 100:1 and
  ii. 3-methyl-butanol and 2-methyl-butanol are present in a ratio of at least 0.3:1.

In such C5 alcohol mixture the ratio of 3-methyl-butanol to 2-methyl-butanol is preferably at least 0.5:1, more preferably at least 1:1, yet more preferably at least 10:1 and most preferably at least 20:1. For example the ratio is preferably in the range 0.3:1-30:1, more preferably 0.5:1-25:1 and most preferably 1:1-20:1. The ratio of n-pentanol to 2-methyl-butanol is preferably in the range 5:1-50:1, more preferably 8:1-40:1, yet more preferably 10:1-35:1 such as 15:1-35:1, and most preferably 20:1-30:1.

In a further embodiment the invention also provides a $C_5$ acid mixture consisting essentially of normal and mono-methyl branched acids and comprising n-pentanoic acid, 2-methyl-butanoic acid and 3-methyl-butanoic acid wherein
  i. n-pentanoic acid and 2-methyl-butanoic acid are present in a ratio from 3:1 to 100:1 and
  ii. 3-methyl-butanoic acid and 2-methyl-butanoic acid are present in a ratio of at least 0.3:1.

In such C5 acid mixture the ratio of 3-methyl-butanoic acid to 2-methyl-butanoic acid is preferably at least 0.5:1, more preferably at least 1:1, yet more preferably at least 10:1 and most preferably at least 20:1. For example the ratio is preferably in the range 0.3:1-30:1, more preferably 0.5:1-25:1 and most preferably 1:1-20:1. The ratio of n-pentanoic acid to 2-methyl-butanoic acid is preferably in the range 5:1-50:1, more preferably 8:1-40:1, yet more preferably 10:1-35:1 such as 15:1-35:1, and most preferably 20:1-30:1.

The invention therefore also provides for mixtures of valeraldehydes that are novel, as produced by the rhodium based hydroformylation of raffinate-1 streams characterised by significant conversions of isobutylene. These valeraldehyde mixtures are characterised by a low content of $C_5$ alcohols, being 30% or less by weight, preferably 16% or less, more preferably 6% or less, most preferably 3% or less. They are also characterised by a significant presence of 3-methyl-butanal or "isovaleraldehyde", generally being below 96%, 92% or 80%, but at a minimum of 10% or higher, more typically 20% or higher, preferably 24% or above, more preferably 26% or higher, most preferably 36% or higher. The remainder of the mixture is primarily composed of n-valeraldehyde and 2-methyl-butyraldehyde. Depending on the choice of phosphorus ligand, the relative ratio of these two can differ between 3:1 normal-to-branched, up to 30 or even 40:1 normal-to-branched ratio. The presence of 2-methyl-butyraldehyde can therefore be low, like 1.5%, or 2% by weight, up to 3 or 4% by weight, or it can be more significant, like 6% or 7% by weight, up to 9 or 10% by weight. N-valeraldehyde presence in the mixtures can conversely be as low as 50-55% by weight, or can be higher at around 70-75%, or even higher still, at 78-84% by weight.

These aldehyde mixtures can be submitted to aldolisation, as such, or after partial (or complete) separation of the branched valeraldehydes from n-valeraldehyde. 3-methyl-butyraldehyde is able to participate in aldolisation, and in two ways as shown below, as it has two alpha hydrogens to the carbonyl bond. The same applies to n-valeraldehyde, but not to 2-methyl-butyraldehyde. An aldolisation of a mix of the three valeraldehydes will therefore produce a mixture of the following enals. The reactions are described in the sequence of the expected rate of aldolisation:

Fastest
n-valeraldehyde+n-valeraldehyde→2-(n)-propyl-2-heptenal (1+1)
Slower
2-Me-butanal+n-valeraldehyde→2-(n)-propyl-4-methyl-2-hexenal (1+2)
3-Me-butanal+n-valeraldehyde→2-(n)-propyl-5-methyl-2-hexenal (1+3)
n-valeraldehyde+3-Me-butanal→2-isopropyl-2-heptenal (3+1)
Slowest
2-Me-butanal+3-Me-butanal→2-isopropyl-4-methyl-2-hexenal (2+3)
3-Me-butanal+3-Me-butanal→2-isopropyl-5-methyl-2-hexenal (3+3)

The production of C10 aldehydes by the aldol condensation of $C_5$ aldehydes produced from feeds with low levels of isobutylene is described in U.S. Pat. No. 6,340,778 and WO 03/029180, and these processes can be used in the present invention.

The present invention therefore further provides an unsaturated aldehyde mixture comprising: 2-isopropyl-2-heptenal; 2-propyl-2-heptenal; 2-propyl-5-methyl-2-hexenal; 2-propyl-4-methyl-2-hexenal and 2-isopropyl-4-methyl-2-hexenal containing at least 20% 2-propyl-2-heptenal and wherein the ratio of the combined amount of 2-isopropyl-2-heptenal and 2-propyl-5-methyl-2-hexenal to the combined amount of 2-propyl-4-methyl-2-hexenal and 2-isopropyl-4-methyl-2-hexenal is at least 0.3. Such ratio is preferably at least 0.5, more preferably at least 1.0, yet more preferably at least 10 and most preferably at least 20. For example the ratio is preferably in the range 0.3-30, more preferably 0.5-25 and most preferably 1-20.

Such unsaturated aldehyde mixture may be hydrogenated selectively to saturate only the C=C double bond, to the equivalent saturated aldehyde mixture, using methods described below.

In a further embodiment the invention therefore provides an aldehyde mixture comprising: 2-isopropyl heptanal; 2-propyl heptanal; 2-propyl-5-methyl hexanal; 2-propyl-4-methyl hexanal and 2-isopropyl-4-methyl hexanal containing at least 20% 2-propyl heptanal and wherein the ratio of the combined amount of 2-isopropyl heptanal and 2-propyl-5-methyl hexanal to the combined amount of 2-propyl-4-methyl hexanal and 2-isopropyl-4-methyl hexanal is at least 0.3. Such ratio is preferably at least 0.5, more preferably at least 1.0, yet more preferably at least 10 and most preferably at least 20. For example the ratio is preferably in the range 0.3-30, more preferably 0.5-25 and most preferably 1-20.

Alternatively the unsaturated aldehyde mixture may be hydrogenated selectively to saturate only the C=O double bond, to the equivalent unsaturated alcohol mixture. Osmium, rhenium and particularly platinum (possibly in an inhibited form) are suitable hydrogenation catalysts herefore.

In yet a further embodiment the present invention therefore provides an unsaturated alcohol mixture comprising: 2-isopropyl-2-heptenol; 2-propyl-2-heptenol; 2-propyl-5-methyl-2-hexenol; 2-propyl-4-methyl-2-hexenol and 2-isopropyl-4-methyl-2-hexenol containing at least 20% 2-propyl-2-heptenol and wherein the ratio of the combined amount of 2-isopropyl-2-heptenol and 2-propyl-5-methyl-2-hexenol to the combined amount of 2-propyl-4-methyl-2-hexenol and 2-isopropyl-4-methyl-2-hexenol is at least 0.3. Such ratio is preferably at least 0.5, more preferably at least 1.0, yet more preferably at least 10 and most preferably at least 20. For example the ratio is preferably in the range 0.3-30, more preferably 0.5-25 and most preferably 1-20.

The condensation of two molecules of an aldehyde to form an aldol, usually followed immediately by dehydration, to form an unsaturated aldehyde with twice the original number of carbon atoms (or the sum of the carbon atoms of two different aldehydes in a cross-aldolisation) is well known, as are the conditions required to effect the condensation. In general, the reactants may be either in the vapour or liquid phase, at moderately elevated temperatures, e.g., from 40° C. to 200° C., and pressures, e.g., from 0.01 to 2 MPa, preferably from 0.1 to 2 MPa. The reaction is generally carried out in the presence of a catalyst, which may be solid or liquid, and either acidic or, preferably, basic. Although organic bases may be used, a, preferably strong, inorganic base, for example an alkali metal hydroxide or carbonate, is preferred, advantageously in the form of an aqueous solution. In other embodiments a solid catalyst, e.g., a metal oxide, especially a titanium or magnesium oxide, may be used. The above conditions apply generally to the aldol process steps of the present invention; under the preferred conditions dehydration is very fast and essentially complete.

If it is desired to make the saturated $C_{10}$ aldehyde from the immediate product of the aldolisation, further hydrogenation may be effected as described above. This procedure is conveniently also used if the desired end product is the corresponding mixture of branched C10 acids, produced by oxidation of the $C_{10}$ aldehyde.

If, however, the desired product is the saturated alcohol mixture, then more vigorous hydrogenation conditions may if desired be employed, hydrogenation of the ethylenic unsaturation and reduction of the carbonyl group taking place at the same time. For this purpose, the reaction may be carried out under conditions and in the presence of catalyst systems known per se. For example, the catalyst may be Ni, Raney Ni, Pt or Pd, partially reduced copper oxides, copper/zinc oxides, copper chromite, the copper-based catalyst advantageously being used in combination with cobalt or nickel catalysts; Ni/Mo; Co/Mo or Mo on carbon, optionally in their sulphided form. Any of the above catalysts may be used alone or in combination; nickel is the preferred catalyst. The conditions may include, for example, a hydrogen pressure from 2 to 30 MPa and a temperature in the range of 100 to 240° C.

Hydrogenation of these $C_{10}$-enal mixtures, by methods known in the art, will produce the mixture of the corresponding alcohols. Selective hydrogenation of these enal mixtures, by methods also known in the art, e.g. as disclosed in U.S. Pat. No. 6,090,986 applied on 2-methyl-2-pentenal, will produce the mixture of the corresponding saturated aldehydes. These can then be further hydrogenated to the corresponding alcohols, but are even more interesting as intermediates for oxidation, by methods also known in the art, catalytic or non-catalytic, with oxygen or air or using another oxygen donor, to the corresponding mixture of carboxylic acids. Alternatively, these aldehydes can be used as fragrance components by themselves, or as intermediates for other fragrance and fine chemical components, like amines. The alcohols and acids are of interest e.g. as feedstocks for esterification, sulfation or alkoxylation possibly followed by sulfation.

Certain mixtures of these $C_{10}$-enals, or their corresponding alcohols and acids, and their derivatives are considered novel compounds as the rhodium-based hydroformylation product of isobutylene has previously not been made together with the hydroformylation product of butene-1 and/or butene-2. This is because isobutylene has for the last 2-3 decades had a higher value into Methyl tertiary Butyl Ether (MtBE) and Ethyl tertiary Butyl Ether (EtBE) as gasoline oxygenates and octane boosters. These novel $C_{10}$ aldehydes, alcohols and acids, or their derivatives, could find use, and benefits, in end-uses such as plasticisers, surfactants, synlubes, fuel additives, adhesives, fire retardants, fragrances and metal salts.

The invention therefore further provides an alcohol mixture comprising: 2-isopropyl heptanol; 2-propyl heptanol; 2-propyl-5-methyl hexanol; 2-propyl-4-methyl hexanol and 2-isopropyl-4-methyl hexanol containing at least 20% 2-propyl heptanol and wherein the ratio of the combined amount of 2-isopropyl heptanol and 2-propyl-5-methyl hexanol to the combined amount of 2-propyl-4-methyl hexanol and 2-isopropyl-4-methyl hexanol is at least 0.3. Such ratio is preferably at least 0.5, more preferably at least 1.0, yet more preferably at least 10 and most preferably at least 20. For example the ratio is preferably in the range 0.3-30, more preferably 0.5-25 and most preferably 1-20.

In a further embodiment the invention provides an acid mixture comprising: 2-isopropyl heptanoic acid; 2-propyl heptanoic acid; 2-propyl-5-methyl hexanoic acid; 2-propyl-4-methyl hexanoic acid and 2-isopropyl-4-methyl hexanoic acid containing at least 20% 2-propyl heptanoic acid and wherein the reaction of the combined amount of 2-isopropyl heptanoic acid and 2-propyl-5-methyl hexanoic acid to the combined amount of 2-propyl-4-methyl hexanoic acid and 2-isopropyl-4-methyl hexanoic acid is at least 0.3. Such ratio is preferably at least 0.5, more preferably at least 1.0, yet more preferably at least 10 and most preferably at least 20. For example the ratio is preferably in the range 0.3-30, more preferably 0.5-25 and most preferably 1-20.

The mixtures of $C_{10}$-enals, their corresponding mixtures of saturated aldehydes, alcohols and acids derived from them, including the further derivatives of those, will thus be characterised in the presence of the aldol products of 3-methyl-butyraldehyde. At the enal level, this means that 2-(n)-propyl-5-methyl-2-hexenal and/or 2-isopropyl-2-heptenal will each independently be present in the mixture for 2% by weight or more, preferably 3% or more, more preferably 5% or more, even more preferably 6% or more, up to 10% or more, and even 11 or 12% by weight. Also 2-isopropyl-4-methyl-2-hexenal and 2-isopropyl-5-methyl-2-hexenal can be present, but are expected to be present at a lower level at about 0.05% by weight or higher, possibly 0.1% by weight or 0.5%, up to 2 to 2.5% by weight. The remainder of the $C_{10}$ component mixture is composed of the other aldol products or derivatives, which at the enal level is primarily 2-propyl-2-heptenal, and this at levels of 74% or above, possibly 86% or above, as high as 91% or 92% by weight. However, if a portion of the n-valeraldehyde is separated off before the aldolisation step, the presence of 2-propyl-2-heptenal or its equivalent will be correspondingly lower and the other components, incorporating branched valeraldehydes, will be correspondingly higher. The resulting content of 2-propyl-2-heptenal may then be as low as 60%, even lower at 50%, or still lower at 40% by weight on the basis of the total weight of the $C_{1-10}$-enals present in the mixture. The compositions of the corresponding aldehydes, alcohols and/or acid derivatives will be correspondingly leaner in the 2-propylheptyl isomer.

As a result of aldolisation, the invention also provides for aldehyde products containing mixtures of various aldol products of the various valeraldehydes. In other words, the $C_5$ aldehyde products of this invention can be aldolized to form a mixture of $C_{10}$ aldehydes, particularly a mixture of $C_{10}$-enals. In one embodiment, there is provided an aldehyde mixture comprising at least 85 wt % more preferably at least 90 wt % 2-propyl-2-heptenal, based on total amount of aldehydes in the mixture. Preferably, the aldehyde mixture comprises at least 92 wt % 2-propyl-2-heptenal, more preferably at least 94 wt % 2-propyl-2-heptenal, and most preferably at least 96 wt % 2-propyl-2-heptenal, based on total amount of aldehydes in the mixture.

In one embodiment, the aldolized product contains a low amount of 2-(n)-propyl-4-methyl-2-hexenal. The amount of 2-(n)-propyl-4-methyl-2-hexenal present in the aldehyde mixture should be not greater than 2 wt %, based on total amount of aldehydes in the mixture. Preferably, the aldehyde mixture comprises not greater than 1.9 wt % 2-(n)-propyl-4-methyl-2-hexenal, more preferably not greater than 1.8 wt %, and most preferably not greater than 1.7 wt % 2-(n)-propyl-4-methyl-2-hexenal, based on total amount of aldehydes in the mixture.

In general, the aldehyde product that is formed in the aldolisation process will contain a measurable quantity of 2-isopropyl-2-heptenal. It is desirable, however, that the aldehyde composition contain not greater than 2 wt % 2-isopropyl-2-heptenal, based on total amount of aldehydes in the mixture. Preferably, the aldehyde composition contains not greater than 1.9 wt % 2-isopropyl-2-heptenal, more preferably not greater than 1.8 wt % 2-isopropyl-2-heptenal, and most preferably not greater than 1.7 wt % 2-isopropyl-2-heptenal, based on total amount of aldehydes in the mixture. Generally, the aldehyde composition will contain at least 0.1 wt %, or 0.5 wt % or 1 wt % or 1.5 wt %, 2-isopropyl-2-heptenal, based on total amount of aldehydes in the mixture.

The aldehyde mixtures of the invention (e.g., the $C_5$ and $C_{10}$ aldehyde mixtures) can be used as fragrance components by themselves or as intermediates for other fragrance and fine chemical components, like amines.

The C10 derivatives are of particular potential commercial relevance. Two $C_5$ aldehydes will combine to a $C_{10}$ aldol condensation product, which most often dehydrates to the unsaturated aldehyde or "enal". Not all combinations are possible, only the following isomers will form to any decent extent:

TABLE 4

Aldol products formed from C5 aldehydes

| # | C10 enal | Shortcode |
|---|---|---|
| 1 | 2-propyl-2-heptenal | 2ph |
| 2 | 2-(n)-propyl-4-Me-hexenal | 2p4mh |
| 3 | 2-(n)-propyl-5-Me-hexenal | 2p5mh |
| 4 | 2-isopropyl-2-heptenal | 2iph |
| 5 | 2-isopropyl-4-Me-2-hexenal | 2ip4mh |
| 6 | 2-isopropyl-5-Me-2-hexenal | 2ip5mh |

Isomers numbered 3, 4, 5 and 6 will be characteristic from the hydroformylation of isobutylene-based products. Raffinate-2 based products will give almost exclusively isomers 1 and 2.

The aldolisation reactions mentioned above run at different rates. However, any commercial aldolisation process will prefer to force high conversion of all aldehydes, including the branched ones, if necessary by recycling unreacted $C_5$ aldehydes. The compositions of the enal product mixes may therefore be predicted as follows:

TABLE 5

$C_{10}$ product composition mixtures

| | | Ligand family | | | | | | |
|---|---|---|---|---|---|---|---|---|
| | | Phosphines | | | | Phosphites | | |
| | | Feed stream ID | | | | | | |
| C10 product: | # | F1 | F2 | F3 | F4 | F1 | F2 | F3 | F4 |
| 2ph | 1 | 63 | 51 | 66 | 80 | 51 | 25 | 56 | 89 |
| 2p4mh | 2 | 10 | 7 | 11 | 17 | 1 | 0 | 1 | 4 |
| 2p5mh | 3 | 14 | 23 | 11 | 1 | 29 | 45 | 25 | 3 |
| 2iph | 4 | 7 | 11 | 6 | 0.6 | 14 | 22 | 13 | 2 |
| 2ip4mh | 5 | 6 | 7 | 5 | 1 | 4 | 3 | 4 | 2 |
| 2ip5mh | 6 | 0.5 | 1 | 0.3 | 0 | 2 | 4 | 1 | 0 |

If it is desired to maintain a number of options for the use of the saturated $C_{10}$ aldehyde, the present invention also provides for a two-stage hydrogenation of the unsaturated aldehyde, the first stage being carried out in the presence of a mild catalyst, for example, a palladium catalyst as mentioned above, in a first reactor, yielding the saturated aldehyde. This may be further hydrogenated using one of the stronger catalysts mentioned above, for example, Ni, in a second reactor. This procedure has the advantage, in addition to flexibility, of facilitating better control of the hydrogenation reaction which, if carried out in a single reactor from unsaturated aldehyde to saturated alcohol, may give an excessive temperature increase because of the heat released on simultaneous hydrogenation of two bonds. The need to control such a highly exothermic reaction adds to reactor costs.

Oxidation of the saturated aldehyde to the corresponding carboxylic acid may be carried out by any method known per se, i.e., practised in the art or described in the literature. Oxidation is conveniently carried out using oxygen, if desired or required in the presence of a catalyst. As catalyst there may be mentioned a solution containing metallic cations, e.g., copper, cobalt or manganese.

The $C_{10}$ alcohols—and their phthalate ester derivatives, will have particular importance. Hydrogenation and/or oxidation to the $C_{10}$ aldehydes, acids and alcohols will not change the isomer mixture composition. The compositions of the aldehyde, acid and alcohol mixtures can therefore be found in Table 5, by assuming the $C_{10}$ product short code stands for respectively the equivalent given in Table 6.

TABLE 6

$C_{10}$ product isomer names

| Short code | Aldehyde | Acid | Alcohol |
|---|---|---|---|
| 2ph | 2-propyl-heptanal | 2-propyl-heptanoic | 2-propyl-heptanol |
| 2p4mh | 2-Pr-4-Me-hexanal | 2-Pr-4-Me-hexanoic | 2-Pr-4-Me-hexanol |
| 2p5mh | 2-Pr-5-Me-hexanal | 2-Pr-5-Me-hexanoic | 2-Pr-5-Me-hexanol |
| 2iph | 2-iPr-heptanal | 2-iPr-heptanoic | 2-iPr-2-heptanol |
| 2ip4mh | 2-iPr-4-Me-hexanal | 2-iPr-4-Me-hexanoic | 2-iPr-4-Me-hexanol |
| 2ip5mh | 2-iPr-5-Me-hexanal | 2-iPr-5-Me-hexanoic | 2-iPr-5-Me-hexanol |

Wherein:
Me = methyl
Pr = (normal)-propyl
iPr = isopropyl

When the $C_{10}$ alcohol mixtures will be reacted with phthalic anhydride to the diester, the content of true di-2-propylheptyl-phthalate (DPHP) will be of the order of as shown in Table 7. The other di-esters will have at least one alkyl chain that is other than "2ph":

TABLE 7

DPHP content of phthalate derivative

| | Ligand family | | | | | | | |
|---|---|---|---|---|---|---|---|---|
| | Phosphines | | | | Phosphites | | | |
| | Feed stream ID | | | | | | | |
| C10 phthalate | F1 | F2 | F3 | F4 | F1 | F2 | F3 | F4 |
| True DPHP (wt %) | 40 | 26 | 44 | 64 | 26 | 6 | 31 | 79 |

The compositions of these mixtures of $C_{10}$ oxygenates, be it enals, aldehydes, alcohols or acids, may be determined by conventional chromatographic techniques (GC or HPLC), optionally combined with mass spectrometry (GC-MS).

After the hydroformylation step, the unreacted remaining butylenes, together with the butanes that came with the feed and those that were formed as by-product in the process, may be separated off as a by-product stream. This stream may be used in one or more of the conventional ways for using $C_4$ hydrocarbons. These include their use or recycle as steamcracker furnace feed or catalytic cracker feed to produce more ethylene, propylene and other cracking products or gasoline components, as feed or recycle to a reformer or a partial oxidation or an autothermal reforming unit to produce synthesis gas, which is potentially useful in the hydroformylation step described before, as LPG blend stock, optionally after further hydrogenation treatment, as alkylation feed, either as such or after full or partial saturation, in which case the increased isobutane content is beneficial to the yield and product quality of the alkylation process. After hydrogenation, the resulting butane streams may also be used or sold, as such or after separation of the normal butane from the isobutane, e.g. as specialty solvents or propellants for spray cans or as blowing agents for foam production.

In one embodiment, the butene stream is hydroformylated (i.e., catalytically reacted with carbon monoxide and hydrogen) to convert at least 15 wt % of the butene-2 to aldehyde product. Preferably, the butene stream is hydroformylated to convert at least 20 wt % of the butene-2, more preferably at least 25 wt % of the butene-2.

The aldehydes, alcohols, acids, and other derivatives of this invention can also be used as plasticizers, surfactants, synlubes, fuel additives, adhesives, fire retardants, refrigerant oils and metal salts. In the case of refrigerant oils, one or more of the alcohols or acids of the invention are esterified, and the resulting ester composition is combined with a refrigerant, particularly a fluorohalogen, to form a refrigerant working fluid. The specific compounds in the mixtures of aldehydes (including enals), alcohols, acids, or esters can be determined by conventional chromatographic techniques, such as gas chromatography (GC) or high pressure liquid chromatography (HPLC). Mass spectrometry (MS), optionally integrated with chromatography, can also be used.

The $C_{10}$ acids produced by the process of the invention have utility in the manufacture of alkyd resins, synthetic lubricants and refrigerant oils. The esters of the $C_{10}$ acids with monohydric alcohols, especially alkanols, having at least 6 carbon atoms, especially from 6 to 24, and more especially from 6 to 12, carbon atoms, have especial utility as lubricants and lubricant components. Also especially useful in this field are the esters of the $C_{10}$ acids with polyhydric alcohols, i.e., those containing at least two hydroxy groups, for example, pentaerythritol, di(pentaerythritol), tri(pentaerythritol); trimethylolethane, trimethylolpropane, trimethylolbutane, and dimers and trimers thereof; and neopentylglycol.

The invention accordingly also provides an ester of a monohydric alcohol having at least 6 carbon atoms, especially from 6 to 24, more especially from 6 to 12, carbon atoms, and such an acid mixture. The invention further provides an ester of a polyhydric alcohol and such an acid mixture.

The acid derivatives, especially their esters, have especial utility in providing components for biodegradable lubricant systems. Oxidatively stable lubricants may be made by partial esterification of a polyol with the $C_{10}$ acid, i.e., esterification leaving an unreacted hydroxy group in the molecule. The metal salts of the acid have utility as catalysts, paint dryers, and PVC stabilizers, while the peroxy esters of the acid are useful as polymerization initiators.

The $C_{10}$ aldehydes are valuable intermediates, especially in the manufacture of $C_{10}$ amines, ether amines, and components for the fragrance industry, for example, through condensation with benzaldehyde.

As indicated above, the saturated $C_{10}$ alcohols produced by the process of the invention, themselves have utility as processing aids in the thermoplastics and textile industries and as solvents for coatings and paints. They are useful as intermediates in the manufacture of ethers, for example, ethoxylate and other detergent bases such as sulfates and alkoxysulfates. They are especially valuable as intermediates in the manufacture of esters suitable for use as solvents, paint coalescers, plasticizers, adhesives, viscosity index improvers, synthetic lubricants, lubricant components, hydraulic fluids, cetane improvers, drilling fluids, thermoplastic and textile processing aids, polymerizable monomers (e.g., with acrylic and methacrylic acids) and fragrances, by reaction with appropriate acids, for example, by reaction with monobasic or polybasic, e.g., tribasic or more especially dibasic acids, or where appropriate derivative of the acids, e.g., anhydrides, or by transesterification with other, e.g., methyl, esters.

The acid may be inorganic or organic; if the latter, carboxylic acids are preferred. Among organic acids, aromatic acids are preferred for plasticizer manufacture, although aliphatic acids are also employed. As examples of acids, acetic, and its homologues, e.g., propionic, acids, acrylic, neodecanoic, lauric, stearic, iso-stearic, erucic, phthalic (1,2-benzenedicarboxylic), isophthalic, terephthalic, adipic, fumaric, azelaic, sebacic, trimellitic, pyromellitic, benzoic, cyclohexanoic, cyclohexanoic dibasic, tall oil, napthenic and napthalene-type acids, carbonic, phosphoric and phosphorous, acids and $C_6$ to $C_{13}$ oxo and neo acids generally may be mentioned. Esters with monobasic and dibasic acids are preferred for lubricants and lubricant components; advantageously the resulting esters contain from 15 to 40 carbon atoms; adipates and phthalates are especially preferred for lubricant manufacture.

The invention accordingly also provides an ester of the alcohol mixture of this invention with a polybasic acid, especially an ester with a dibasic acid. The invention also provides an ester of a polybasic acid in which all the acid groups are esterified by the alcohol mixture of this invention, especially a dibasic acid both acid groups of which are thereby esterified. Among specific esters provided by the invention there may be mentioned, esters of 1,2-benzenedicarboxylic and hexanedioic acids and the tris ester of 1,2,4-benzenetricarboxylic acid, which find use as plasticisers for polymers particularly polyvinyl chloride. The phthalate ester also has advantages in the manufacture of automotive sealant compositions in part because of their increased viscosity and enhanced viscosity stability of the composition. Its oxidative stability, stain resistance and foaming properties are comparable with those of Jayflex DINP®, di-isononylphthalate of ExxonMobil Chemical Company.

The esters may be produced by methods known per se or described in the literature from the alcohol and the relevant acid or, preferably, where appropriate, the anhydride, optionally in the presence of a solvent. Elevated temperatures and reduced pressures are generally employed to drive the reaction toward completion by removal of the water produced. Catalysts may be employed. Suitable catalysts include, for example, a titanium catalyst e.g., a tetraalkyl titanate, especially tetra-iso-propyl or tetraoctyl ortho titanate, or a sulphonic acid, e.g., p-toluene sulphonic acid or methylsulphonic acid. Any catalyst present in the reaction product may be removed by alkali treatment and water washing. Advantageously, the alcohol is used in slight, e.g., from 10 to 25%, molar excess relative to the number of acid groups in the acid.

The esters may be used as a plasticizer for numerous polymers, for example, cellulose acetate; homo- and copolymers of aromatic vinyl compounds e.g., styrene, or of vinyl esters with carboxylic acids e.g., ethylene/vinyl acetate copolymers; halogen-containing polymers, especially vinyl chloride homo- and copolymers, more especially those copolymers with vinyl esters of carboxylic acids, esters of unsaturated carboxylic acids e.g., methacrylates, and/or olefins; nitrile rubbers; and post-chlorinated vinyl chloride polymers. Poly(vinyl chloride) is of especial interest.

The proportion of plasticizer may vary within wide limits, but is generally 10 to 200 parts by weight per 100 parts of polymer, more especially 20 to 100 parts per 100.

The esters of the invention may be used alone as plasticizer, or in admixture with other plasticizers, for example, dibutyl, dipentyl, dihexyl, diheptyl, dioctyl, dinonyl, didecyl, diundecyl, didodecyl, ditridecyl phthalates, trimellitates or adipates, each time including the normal and branched alkyl chain equivalents, or butyl benzyl phthalate, or mixtures thereof. They may also or instead be used with a secondary plasticizer, e.g., a chlorinated paraffin, Texanol isobutyrate, or a processing oil. If used in admixture, it is the total proportion of plasticizer that is advantageously within the ranges given above.

The plasticized polymeric compositions of the invention may be made up in numerous forms and have various end-uses. For example, they may be in the form of a dryblend, a paste, or a plastisol, depending on the grade of the resin employed. They may be used, for example, as coatings, in dipping, spraying, injection or rotational moulding, extrusion, or as self-supporting films and sheets, and may readily be foamed. End uses include flooring materials, wall coverings, moulded products, upholstery materials, leather substitutes, electrical insulation, especially wire and cable, coated fabrics, toys, and automobile parts.

The invention is illustrated by reference to the accompanying Examples which illustrate the extent to which isobutylene can be converted by rhodium hydroformylation and also the hydroformylation of mixed butene feeds one of which was prepared to represent a butene feed from an oxygenate to olefin reaction and the other a butene feed from steamcracking of petrochemical feedstocks followed by selective hydrogenation of butadiene. The latter is called here raffinate 1.5 for convenience.

EXAMPLES

The following procedure was employed in Examples 1 to 6.

Hydroformylation was carried out in a standard half liter zipperclave reactor from Autoclave Engineers. Mixing occurred with an air driven stirrer with speed controlled at 2000 revolutions per minute. The mixer had a six bladed impeller that guaranteed a strong mixing between the gas and the liquid phase. Baffles inside the reactor prevented vortex formation and created back mixing. The reaction temperature was controlled at 95° C.+/−1° C. Pressure was controlled at 10 barg+/−0.1 bar. Synthesis gas (48% $H_2$ and 52% CO) was delivered from a calibrated high pressure storage cylinder equipped with a pressure transmitter allowing pressure reading at 0.01 bar accuracy.

Each experiment started with a catalyst solution of the following composition:
Ligand A=0.244 g
Tetraglyme (solvent)=191.2 g
Rhodium=0.011 g
The rhodium was dosed using rhodium carbonyl acetylacetonate as catalyst precursor.
The catalyst solution contained 56 wtppm rhodium.

The catalyst solution was transferred into the reactor. The reactor was purged several times with syngas to remove air. The reactor content was then heated up to 95° C. under 2 barg syngas pressure.

Examples 7 to 10 were performed in a similar manner using triphenylphosphine (TPP) as a ligand at 110° C.

Once the desired reaction temperature was reached, about 0.05 mol of olefin was injected in the catalyst solution by means of synthesis gas and at the same time of the substrate injection the pressure was adjusted to 10 barg. Immediately after the olefin injection and pressure adjustment, the progress of the reaction was followed by measuring the rate of gas consumption, indicated by the pressure decay in the high pressure syngas storage cylinder.

The test duration was 3 hours. At the end of the reaction the gas supply was stopped and the reactor was cooled down to room temperature. Then a gas sample was taken from the gas phase inside the reactor and analysed on a HP6890 gas chromatograph equipped with a thermal conductivity detector (TCD) detection system and a poraplot Q column of 30 m length, 0.53 mm internal diameter (ID), 10 micrometer film thickness (df). A liquid sample was then withdrawn from the reactor into a cooled sample vial and analysed for product composition by gas chromatography using a HP6890 gas chromatograph equipped with a flame ionisation detector (FID) detection system and a WCOT Ultimetal column of 10 m*0.53 mm ID, 0.17 micrometer df HPSimdistC. For the determination of dimethylether a second analysis was carried out over a chrompack, CP Wax 52 fused silica of 50 m*0.25 mm ID, 0.2 micrometer df. For the determination of acetaldehyde a second analysis was carried out over a capillary column HP-FFAP polyethyleneglycol TPA (terephthalic acid) of 50 m*0.32 mm ID, 0.5 micrometer df.

Sulphur analyses of the products were done on a HP6890 gas chromatograph equipped with a fused silica column of 30 m*0.32 ID*5 micrometer CPSIL5CB and a model 355 flameless sulphur chemoluminescence detector from Sievers.

Finally the reactor was depressurized and the liquid recovered and weighed. From the weight of the product, its composition and the composition of the off-gas, a substrate molar end-conversion was calculated. The conversion at any given moment could be calculated pro-rata the pressure drop at that moment, the measured end-conversion and the total pressure drop achieved at the end of the experiment.

The results obtained were as follows.

| | Ex 1 | Ex 2 | Ex 3 | Ex 4 | Ex 5 | Ex 6 | Ex 7 | Ex 8 | Ex 9 | Ex 10 |
|---|---|---|---|---|---|---|---|---|---|---|
| Feed (grams) | | | | | | | | | | |
| i-butene | | | 4.600 | 0.968 | 0.180 | 0.164 | | | | 2.7 |
| n-butene-1 | 4.600 | | | 1.804 | 1.215 | 1.107 | 2.7 | 2.7 | | |
| n-butene-2 | | 4.3 | | 1.408 | 2.655 | 2.419 | | | 2.7 | |
| n-butane | | | | 0.176 | 0.360 | 0.328 | | | | |
| i-butane | | | | 0.044 | 0.090 | 0.082 | | | | |
| Ligand A | 0.244 | 0.244 | 0.244 | 0.244 | 0.244 | 0.244 | | | | |
| TPP | | | | | | | 19.84 | 19.84 | 19.84 | 19.54 |
| Rhodium | 0.011 | 0.011 | 0.011 | 0.011 | 0.011 | 0.011 | 0.00576 | 0.00576 | 0.00576 | 0.00576 |
| Tetraglyme | 191.2 | 191.2 | 191.2 | 191.2 | 191.2 | 191.2 | 191.2 | 191.2 | 191.2 | 191.2 |
| Product (grams) | | | | | | | | | | |
| C4 | | 1.271 | | 0.528 | 0.722 | 0.824 | 0.124 | 0.127 | 2.24 | 1.97 |
| 3Me butyraldehyde | | | | 1.109 | 0.041 | 0.052 | | | | 0.45 |
| 2Me butyraldehyde | 0.306 | 0.695 | | 0.356 | 0.114 | 0.206 | 0.663 | 0.717 | 0.59 | |
| n-valeraldehyde | 5.773 | 4.524 | 0.519 | 3.867 | 3.644 | 3.813 | 3.314 | 3.503 | 0.13 | 0.17 |
| Ligand | 0.420 | 0.104 | 0.168 | 0.415 | 0.214 | 0.227 | | | | |
| Valeric acid | 0.000 | 0.000 | 0.000 | 0.000 | 0.000 | 0.000 | 0.041 | 0.042 | 0.00 | 0.00 |
| Tetraglyme | 189.089 | 189.078 | 188.274 | 189.204 | 189.239 | 187.931 | 180.985 | 183.929 | 186.16 | 188.62 |
| C4 in offgas | 0.003 | 0.003 | 0.003 | 0.003 | 0.003 | 0.003 | 0.003 | 0.003 | 0.29 | 0.45 |

Example 1 n-butene-1 hydroformylation

The conversion was 86%.

Example 2 n-butene-2 (40% cis and 60% trans) hydroformylation

The conversion was 79%.

Example 3 iso-butylene hydroformylation

The conversion was 81.7%. It is believed that the trace of n-valeraldehyde in the product originated from a feed impurity.

Example 4 raffinate 1.5 hydroformylation

The mixture that was used had following composition by weighted blending:
22 wt % isobutylene, 41 wt % n-butene-1, 32 wt % mixed n-butene-2s (cis and trans), 4 wt % n-butane and 1 wt % isobutane The end conversion was 82.9%. The relative break-down of the aldehydes was 20.8% 3-methylbutanal, 6.7% 2-methylbutanal and 72.1% n-valeraldehyde. Based on molar balance the isobutene showed to have reached 74.5% conversion. The cumulative conversion of n-butene-1 and n-butene-2s was 84.5%. There was no evidence by GC of the presence of any pivaldehyde or 2,2-dimethyl propanal.

Example 5

Hydroformylation of Oxygenate to Olefin Based Mixed Butenes

The mixture that was used was obtained by mixing to represent a butene stream that would be obtained from the conversion of methanol to olefins, and had the following composition by weighed blending:
4 wt % isobutene, 27 wt % n-butene-1, 59 wt % mixed n-butene-2s (cis and trans), 8 wt % n-butane, 2 wt % isobutane.

The overall conversion was 67%. The relative break-down of the aldehydes was 3.98% 3-methylbutanal, 2.92% 2-methylbutanal and 93.1% n-valeraldehyde. Based on a molar balance, the isobutene showed to have reached 61.8% conversion. The cumulative conversion of n-butene-1 and n-butene-2s was 69.3%. There was no evidence by GC of the presence of any pivaldehyde or 2,2-dimethyl propanal.

Example 6

Hydroformylation of Oxygenate to Olefin Based Mixed Butenes with Acetaldehyde In this experiment 0.5 wt % of acetaldehyde (1 gram) was injected in the catalyst solution to give a molar ratio of acetaldehyde to rhodium of 211.

A first order reaction rate constant of 0.51 $h^{-1}$ was measured, indicating no decrease in reaction rate compared to the base case of Example 5, where the first order reaction rate constant as measured was 0.47 $h^{-1}$.

The results indicate that acetaldehyde has no inhibiting effect on the hydroformylation rate of mixed butenes in the low pressure rhodium/Ligand A system.

GC analysis of the final products showed 0.47 wt % of acetaldehyde (0.917 gram), indicating that acetaldehyde essentially did not take part in any reaction.

Examples 7 and 8 butene-1 hydroformylation

Two experiments were carried out to provide a base case reaction rate for n-butene-1 hydroformylation with rhodium and triphenyl phosphine as catalyst. The two runs also provided indication about the reproducibility of the experiments.

Examples 9 and 10 butene-2 and iso-butylene hydroformylation

N-butene-2s and isobutene was also tested as substrates in hydroformylation with rhodium and triphenylposphine. Both substrates showed at 110° C. and 10 barg a reaction rate of about 0.05 $h^{-1}$ and reacted therefore about 50 times slower than n-butene-1. The main product components are branched valeraldehydes, while only very little n-valeraldehyde is produced.

Figure 1:
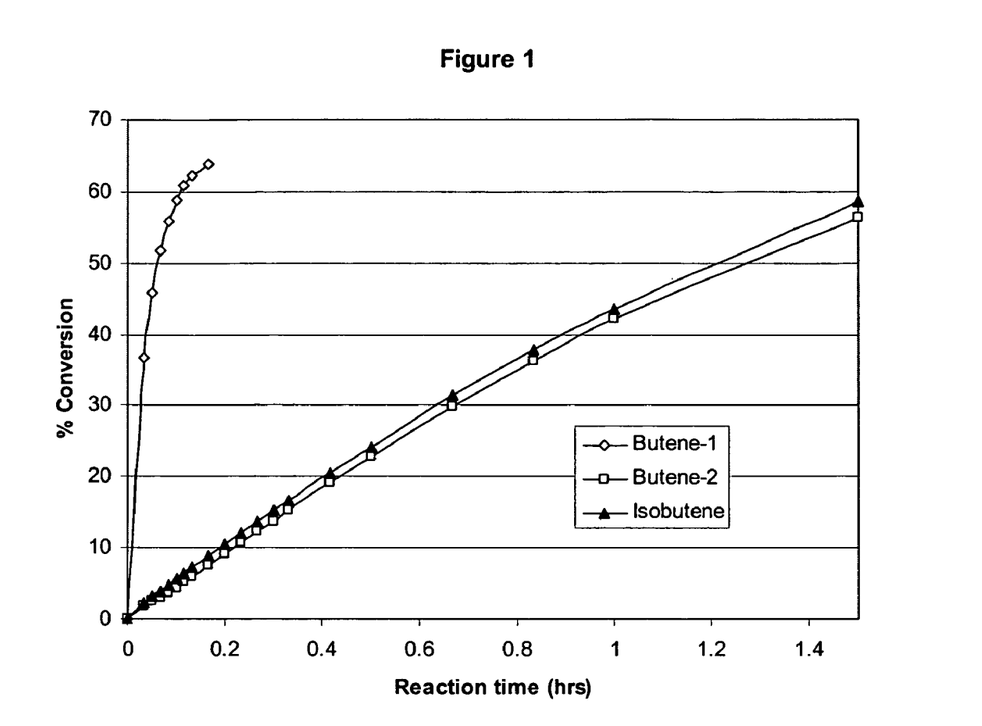
FIG. 1 shows a plot of experimental data from examples set forth herein.

These results show that butene-1 will always react quickly and that by selecting the appropriate conditions (temperature, carbon monoxide partial pressure and residence time), butene-2s and isobutylene can also be made to react, as is illustrated in FIG. 1 which plots the conversions over time achieved in Examples 1, 2 and 3.

The invention claimed is:

1. A process for the production of a $C_5$ aldehyde mixture comprising n-pentanal, 3-methyl-butanal and 2-methyl-butanal wherein
    i. the ratio of n-pentanal to 2-methyl-butanal is from 3:1 to 100:1; and
    ii. the ratio of 3-methyl-butanal to 2-methyl-butanal is at least 0.3:1, the process comprising: hydroformylating a $C_4$ feed comprising at least one normal butene and from 15 wt % to 50 wt % isobutylene in a single liquid phase in the presence of a catalyst comprising a rhodium complex in conjunction with an organophosphorus ligand and under conditions that convert normal butenes and convert at least 30% of the isobutylene to produce a mixture of isomers of valeraldehyde; wherein the process further comprises hydroformylating at a temperature in the range of 50 to 180° C., a total pressure of not more than 10000 kPa, a partial pressure of carbon monoxide of below 5000 kPa, and a partial pressure of hydrogen in the range from 100 to 7000 kPa.

2. The process according to claim 1 wherein the organophosphorus ligand is selected from the group consisting of tertiary organophosphines and organophosphites.

3. The process according to claim 2 wherein the organophosphorus ligand is a bisphosphite ligand of the formula 4. The process according to claim 1 wherein at least 45% of the isobutylene is converted.

5. The process according to claim 4 wherein at least 55% of the isobutylene is converted.

6. The process according to claim 5 wherein at least 60% of the isobutylene is converted.

7. The process according to claim 1 wherein the $C_4$ feed contains from 15 to 50 wt % isobutylene and from 40 to 85 wt % normal butenes.

8. The process according to claim 1 wherein the feed contains from 12% to 30% of butene-1 and from 17% to 40% of butene-2.

9. The process according to claim 1 operated at a carbon monoxide partial pressure of at least 0.2 MPa.

10. The process according to claim 9 operated at a carbon monoxide partial pressure of at least 0.5 MPa.

11. The process of claim 1 wherein the $C_4$ feed is produced by an oxygenate conversion reaction.

12. The process of claim 1 wherein the $C_4$ feed does not require the removal of isobutylene prior to the hydroformylating step.

13. The process of claim 1 wherein the $C_4$ feed does not require the removal of compounds containing sulfur, nitrogen, or chlorine prior to the hydroformylating step.

14. The process of claim 1 wherein the total gas pressure of hydrogen, carbon monoxide and olefinic unsaturated starting compound is more than 5000 kPa.

* * * * *